United States Patent [19]
Allen et al.

[11] Patent Number: 5,672,885
[45] Date of Patent: Sep. 30, 1997

[54] SURFACE DISPLACEMENT DETECTION AND ADJUSTMENT SYSTEM

[75] Inventors: Nicholas Allen, Bedford; Abdu Broudour, West Newton; Sergey Broude, Newton Centre; Eric Chase, Carlisle; Carl Johnson, Tewksbury; Pascal Miller, North Chelmsford; Jay Ormsby, Salem; Arkady Savikovsky, Brookline, all of Mass.

[73] Assignee: QC Optics, Inc., Burlington, Mass.

[21] Appl. No.: 499,822

[22] Filed: Jul. 10, 1995

[51] Int. Cl.[6] .................................................. G01N 21/89
[52] U.S. Cl. ........................ 250/559.3; 250/559.39; 250/559.45; 250/559.04; 356/373; 356/237
[58] Field of Search ........................ 250/201.2, 559.3, 250/559.31, 559.39, 559.45, 559.46, 559.04, 237 G; 356/373, 374, 376, 430, 237

[56] References Cited

U.S. PATENT DOCUMENTS

| | | | |
|---|---|---|---|
| 4,423,331 | 12/1983 | Koizumi et al. | 250/559.45 |
| 4,794,265 | 12/1988 | Quackenbos et al. | 250/559.45 |
| 4,930,115 | 5/1990 | Verboom et al. | 369/59 |
| 4,954,723 | 9/1990 | Takahashi et al. | 250/559.45 |

*Primary Examiner*—Stephone Allen
*Attorney, Agent, or Firm*—Iandiorio & Teska

[57] ABSTRACT

A surface displacement detection system including a detector for detecting displacement of a surface in a direction normal to the surface as the surface revolves; an encoder which divides the surface into N sectors; a signal processor responsive to the detector for calculating the amount of displacement of the surface in each sector of the surface as it revolves; a displacement value look-up table; and a routine for writing to the table a displacement value for each sector once per M revolutions, and an adjustment system including a focussing actuating element, a routine to read displacement value look-up table, a routine to for updating the position of the focussing actuating element for every sector, according to the displacement values stored in the look-up table.

25 Claims, 5 Drawing Sheets

5,672,885

SURFACE DISPLACEMENT DETECTION AND ADJUSTMENT SYSTEM

FIELD OF INVENTION

A surface displacement detection and adjustment system for automatically focusing a laser beam on a rotating surface (e.g., a photolithographic mask), and more particularly to such a system that automatically adjusts itself to account for surface warpage and/or displacement thereby maintaining the focus of the laser beam as the surface rotates.

BACKGROUND OF INVENTION

Glass photolithographic masks or plates comprising a chrome pattern on a glass or quartz substrate are used in the manufacture of thousands of semi-conductor wafers during a production run using a "stepper" printing machine. Therefore, it is critical that the surface of the mask be free of contaminating particles lest the image of the particles repeat as defect on every wafer. Accordingly, the masks are typically inspected first before a production run using very precise equipment shown, for example, in U.S. Pat. Nos. 4,943,734; 4,794,264; 4,794,265; and 5,389,794 incorporated herein by reference.

As a mechanical mask holder/spindle assembly spins the mask, the surface of the mask is illuminated by a laser beam directed to the surface by means of a flat or parabolic mirror or lens and the scattering of the laser beam off the surface is analyzed: the scattering off the surface will be different if a flaw or particle is present than if no flaw or particle is present. The scattering can be analyzed to the point where and a particle or flaw can be classified by size. In order to scan for and detect very small particles (e.g. 0.3 microns in diameter), it is very important that the laser beam be focused to form a very small spot size. Therefore, the distance from the parabolic mirror to the surface must be kept constant. Since the mask may be warped and/or since the mechanical mask holder/spindle assembly may cause displacement of the mask with respect to the parabolic mirror, however, the laser beam may become unfocused on the mask surface. Accordingly, any displacement of the mask must be detected and the mask re-aligned.

Detecting and then updating the mount of displacement of in each sector of the mask surface during each revolution at high rotational speeds, however, requires a complicated, expensive, and very fast digital processing system. Such a system is impractical and cost prohibitive.

SUMMARY OF INVENTION

It is therefore an object of this invention to provide a less complicated system for automatically focusing a laser beam on a rotating surface.

It is a further object of this invention to provide a surface displacement detection and adjustment system which is easy to implement and which requires as input only data concerning the rotation of the surface and data concerning displacement of the surface.

In a photolithographic mask inspection apparatus, there is often displacement of the rotating photolithographic mask with respect to the laser beam focusing mirror due to warpage of the mask and this invention results from the realization that although this displacement must be adjusted during each sector of the mask as it rotates, the flatness of any one sector over a number of rotations will not vary significantly and therefore the displacement value associated with each sector need only be updated after a number of revolutions thereby eliminating the complicated, expensive, and fast digital signal processing required to update the displacement value of each sector during each revolution. The photolithographic mask is rotated on a spindle at 1800 rpm and inspected by a sharply focussed laser beam trace directed to the surface by a parabolic mirror. The spacing between each trace per revolution is approximately 3 microns and yet the profile of a typical mask only varies significantly across the surface every 10 mm to 30 mm.

Therefore, although the parabolic mirror must be adjusted as the mask rotates, the amount of adjustment required for any one sector over a number of revolutions is di minimus and can be kept constant thereby eliminating the complicated signal processing equipment required to update the amount of warpage of each sector during each revolution.

This invention features and depending on the implementation, suitably comprise, include, consist of, or consist essentially of a surface displacement detection system. There are means for detecting displacement of a surface in a direction normal to the surface as the surface revolves; means for dividing the surface into N sectors; means, responsive to the means for detecting, for calculating the amount of displacement of the surface in each sector of the surface as it revolves; a displacement value look-up table; and means, responsive to the means for calculating, for writing to the table a displacement value for each sector once per M revolutions.

Further included is a routine for averaging the present displacement value for a given sector N with the last calculated displacement value for that sector and for writing the avenge to the table for reducing noise and interference.

The means for writing may write the displacement value for all N sectors during one revolution, M-1 revolutions before the next write operation, or alternatively may write a displacement value at a rate of one sector per revolution.

The table has N address spaces and each address space is allocated for a specific sector. There are also means for reading the look up table including means for reading each displacement value stored in the look-up table every revolution and updating the focusing element position for every sector of every revolution according to the look-up table, as the surface revolves.

The means for detecting includes a first grating; a second grating; means for projecting an image of the first grating onto the surface; means for directing a secondary image of the first grating reflected off the surface onto a second grating; and detector means, responsive to the fringe pattern formed after the secondary image passes through the second grating, for detecting displacement of the surface in a direction normal to the surface.

This invention also features a surface displacement detection and adjustment system comprising: a laser beam source and means for focusing the laser beam source on the surface, the means for focusing being adjustable with respect to the surface; means for detecting displacement of the surface in a direction normal to the surface as the surface revolves; means dividing the surface into N sectors; means, responsive to the means for detecting, for calculating the amount of displacement of the surface in each sector of the surface as it revolves; a displacement value look-up table; and means, responsive to the means for calculating, for writing to the table a displacement value for a given sector N once per M revolutions.

The system further includes means for reading the look-up table and for reading each displacement value stored in the look-up table every revolution. There are means responsive to the means for reading, for adjusting the means for focusing on every sector according to said look up table as the surface revolves.

DISCLOSURE OF PREFERRED EMBODIMENT

Other objects, features and advantages will occur to those skilled in the art from the following description of a preferred embodiment and the accompanying drawings, in which.

Figure 1:
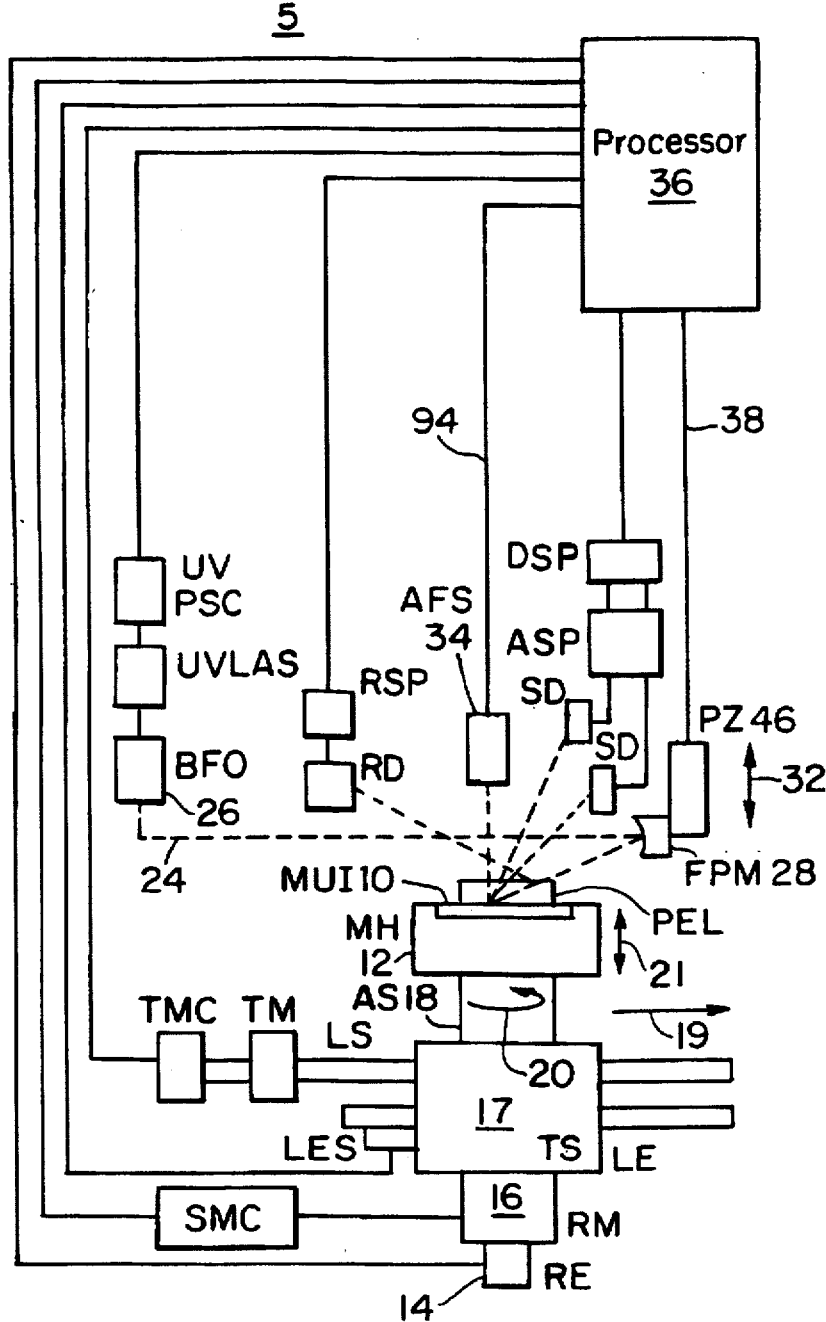
FIG. 1 is a block diagram of a photolithographic mask laser inspection apparatus which incorporates the surface displacement detection and adjustment system according to this invention.

Photolithographic mask inspection system 5, FIG. 1, includes mask holder 12 supporting photolithographic mask 10. Holder 12 is rotated by air spindle 18 in the direction shown by arrow 20. Air spindle 18 is translated in the direction shown by arrow 19 by translation stage 17. A spiral pattern is formed on the surface of mask 10 as shown at 22, FIG. 2, as laser beam 24, FIG. 1, from beam forming optics 26 is directed to the rotating and translating surface of photolithographic mask 10 via parabolic minor 28.

Figure 2:
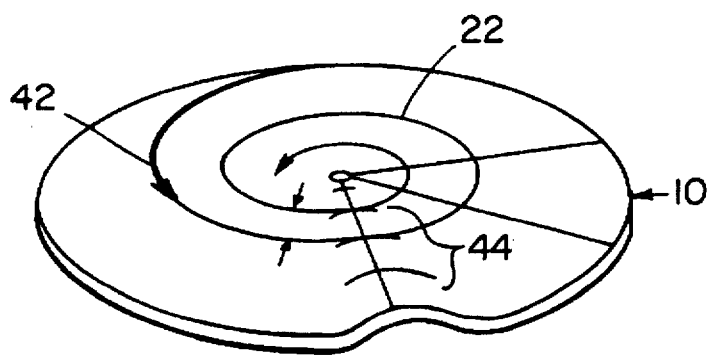
FIG. 2 is a schematic view of a warped photolithographic mask which can be accommodated by this invention.

Due to warpage of the surface of photolithographic mask 10, FIG. 2 as shown at 30, parabolic mirror 28 must be adjusted up and down in the direction shown by arrow 15. 32 in order to maintain the focus of laser beam 24 on the surface of mask 10. Mirror 28 must also be adjusted should air spindle 12 and/or translation stage 17 move in the direction shown by arrow 21. Piezoelectric actuator 40 adjusts mirror 28 up and down in the direction shown by arrow 32 to maintain the proper focus of the laser beam on surface 10 for accurate particle or flaw detection and classification.

Figure 7:
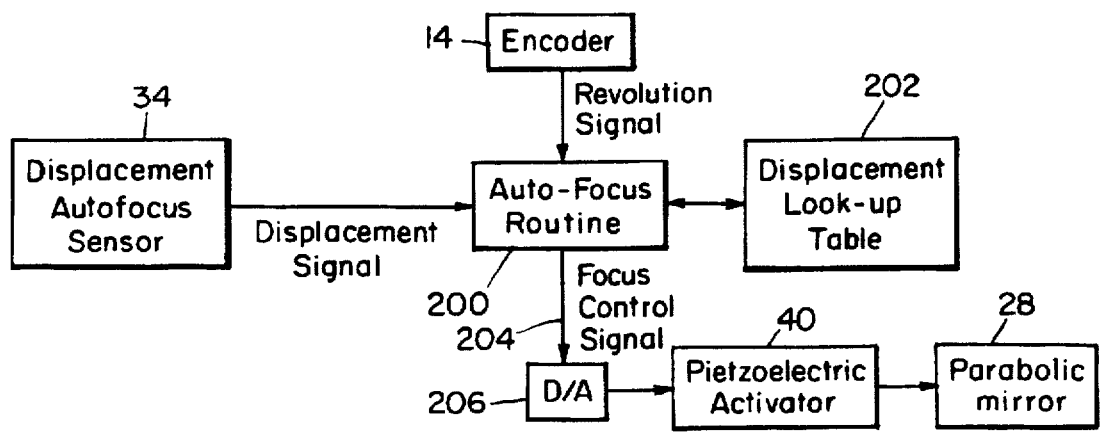
FIG. 7 is a block diagram showing the interface between the autofocus routine of either FIG. 4 or FIG. 6 with the other subsystems of the inspection apparatus device shown in FIG. 1.
Figure 8:
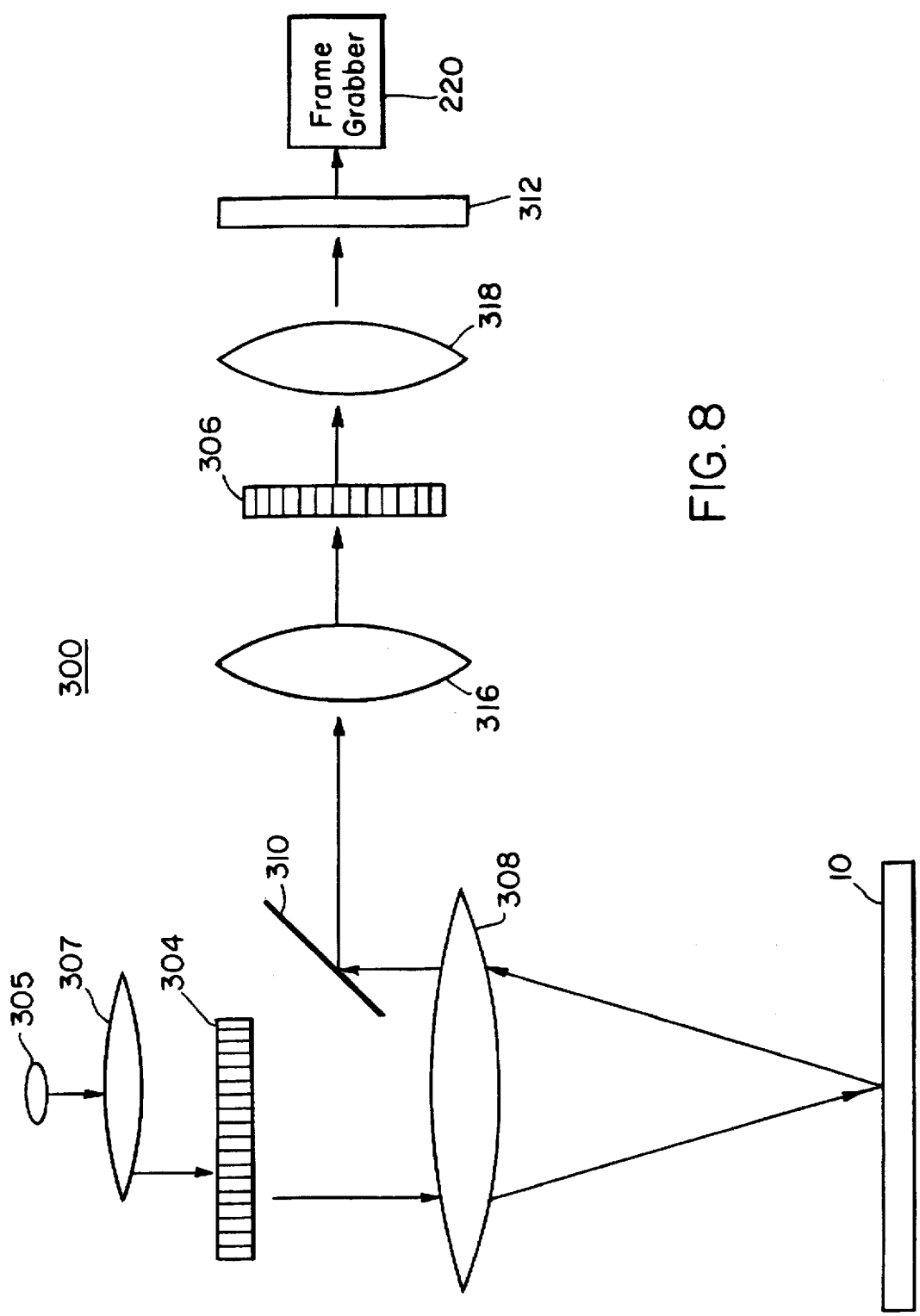
FIG. 8 is a schematic view of the optical assembly of the preferred displacement subsystem shown in FIG. 1 for detecting displacement of a surface.

Autofocus sensor 34 detects any deflection of the surface of photolithographic mask 10 in the direction normal to the surface as explained supra with respect to FIGS. 7 and 8. In summary fashion, a displacement signal is processed via signal processor 36 to determine the amount of displacement in each sector of mask 10 during each revolution. A focus control signal based on the amount of displacement is sent on line 38 to piezoelectric actuator 40 which adjusts parabolic mirror 28 in the direction shown by arrow 32 in real time as photolithographic mask 10 rotates at a speed of 1800 rpm.

Measuring the amount of warpage in each sector during each revolution and then adjusting mirror 40 up and down in each sector during each revolution, however, requires a complicated, expensive, and very fast digital processing system. In this invention, it was realized that the space between each trace of the laser beam on the surface as shown at 42 is approximately 3 microns and yet the profile of the mask only varies significantly across the surface every 10 mm to 30 mm as shown at 44.

Figure 3:
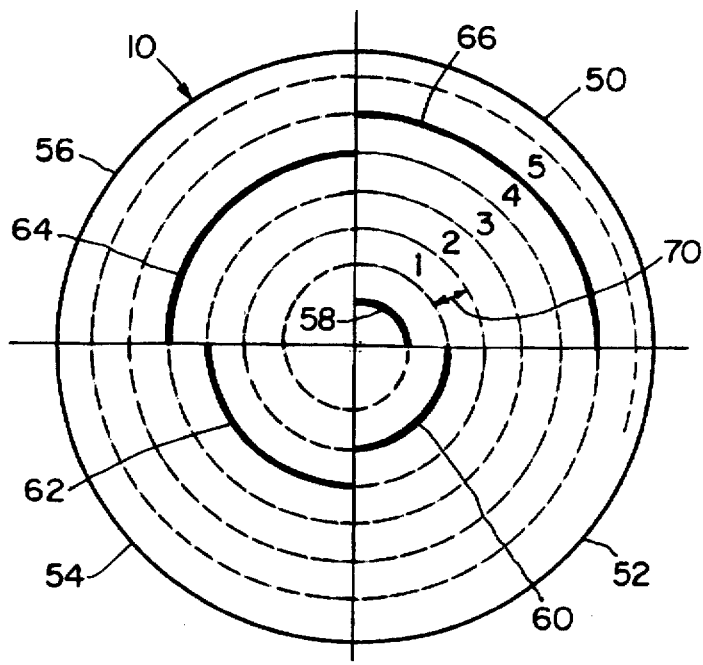
FIG. 3 is a top plan schematic view of a typical trace of a laser beam on a rotating photolithographic mask in accordance with this invention.

Therefore, although parabolic mirror 28 must be adjusted as mask 10 rotates, the amount of adjustment required for any one area or sector over a number of revolutions is di minimus and can be kept constant. This is accomplished as shown in FIG. 3 by dividing the surface of the mask 10 into a number, N, (in this simplified example N=4) sectors 50, 52, 54, and 56. The amount of warpage or surface deflection in each sector is determined, not on each rotation of the surface, but instead only once per M (e.g. M=4) revolutions as shown. Sector 50 is analyzed as shown at 58 during the first revolution, sector 52 is analyzed as shown in 60 during the second revolution, sector 54 is analyzed during the third revolution as shown at 62, and sector 56 is analyzed during the fourth revolution as shown at 64. The first sector 50 is then analyzed again on the fifth revolution and so on. During the analysis of each sector, a displacement value as shown in the table at 68 is stored in look-up table 86, FIG. 4, so that the look-up table is only updated for each sector once per M revolutions of mask 10. This is possible, because as explained above, the distance between successive laser beam traces as shown at 70, FIG. 3 is only 3 microns and yet the profile of surface 10 does not vary significantly over this distance along any one sector. Therefore, the amount of surface variation and hence the displacement value for sector 50 need not be updated until a number of revolutions has occurred. This is important because it only takes about 32 milliseconds for one revolution of surface 10 and the digital signal processing system required to update the displacement value 68 for each sector during each revolution would be very complicated and expensive. By way of example, in this invention, however, displacement value 68 for sector 50 is not updated until after 4 revolutions since the last update as shown at 72. Actually, there are usually 32 instead of 4 sectors.

Figure 4:
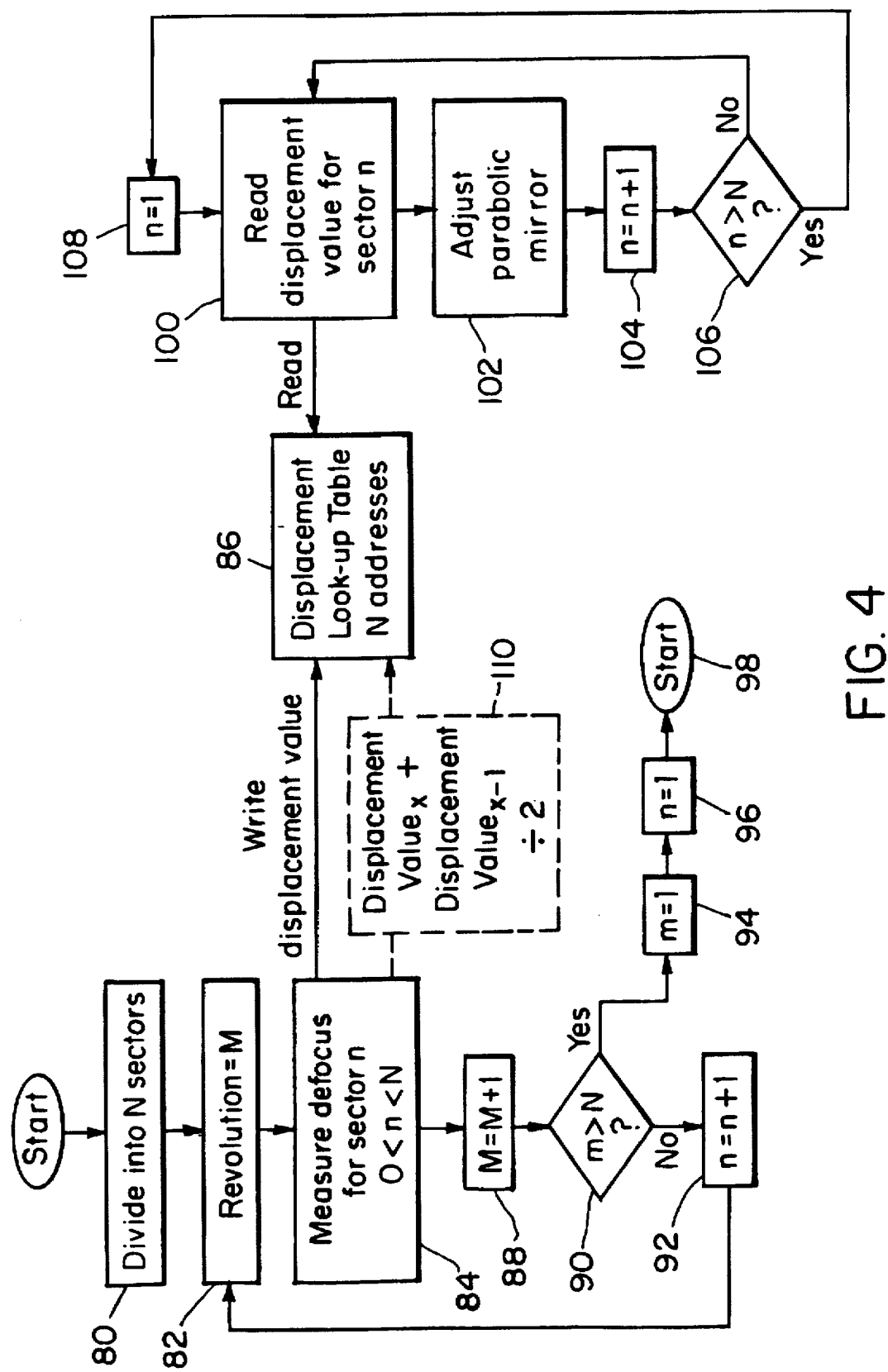
FIG. 4 is a flow chart of the autofocus routine used to automatically focus the laser beam on the rotating surface in accordance with this invention.

As shown in FIG. 4, the surface is divided into N sectors, step 80, preferably between 30–40, and during each revolution, step 82, the focus of the laser beam on that sector is measured for the Nth sector, step 84, and the displacement value written to a displacement look-up table 86 having N address spaces. During the next revolution, step 88, so long as M revolutions have not already occurred, step 90, the Nth sector is updated, step 92 and again the focus value (displacement) for that sector is written to look up table 86. Once there have been M revolutions, the process starts again for the Nth sector, steps 94, 96 and 98. In this way a displacement detection means, such as autofocus sensor 34, FIG. 1, can be operated to write a displacement value for each sector N to the appropriate address in the look-up table only once per M (e.g. 32) revolutions of the surface.

The current displacement value for each sector, step 100, is read, however, during each revolution to adjust parabolic mirror 40, FIG. 1, step 102, FIG. 4 as the laser beam traverses each sector during each revolution of surface 10, steps 104, 106 and 108. To account for noise, successive displacement values may be averaged e.g. by adding the newest displacement value for that sector to the last displacement value and dividing by two as shown in block 110, or by another averaging method.

Figure 5:
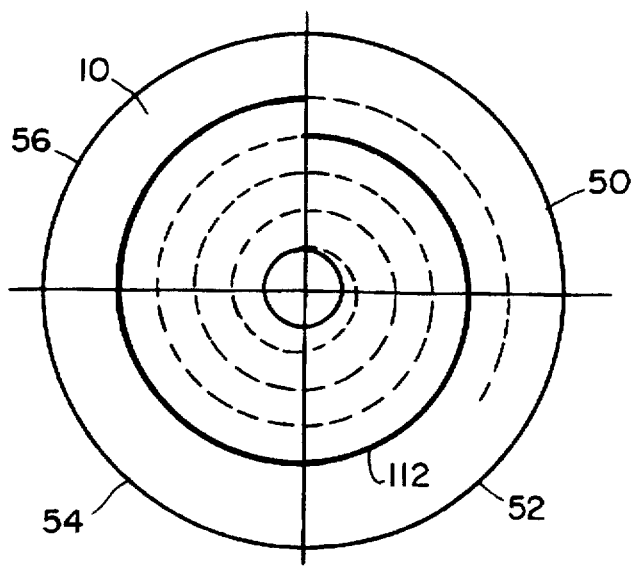
FIG. 5 is a top plan schematic view of another type of trace of a laser beam on a photolithographic mask in accordance with this invention.

The idea of updating the displacement value for each sector only once, for example, per N=4 revolutions as surface 10 rotates can also be accomplished by analyzing sectors 50, 52, 54 and 56 as shown by dark line 112, FIG. 5, all during a single revolution and then waiting three revolutions before analyzing these four sectors again. In general, then, the surface is still divided into N (preferably 32) sectors, step 114, and during a single revolution, step 116, the amount of defocus for each sector is measured, steps 118, 120 and 122 and the results written to a look-up table with N address spaces 124 but then not measured again until M-1 more revolutions, steps, 126 to provide a pause between the updating of the look-up table. During this pause time, other processing activities can occur such as reading the displacement table, step 130, for each sector and adjusting the parabolic mirror, step 132, as required for each sector during each rotation of the surface, steps 134, 136, 138.

Figure 6:
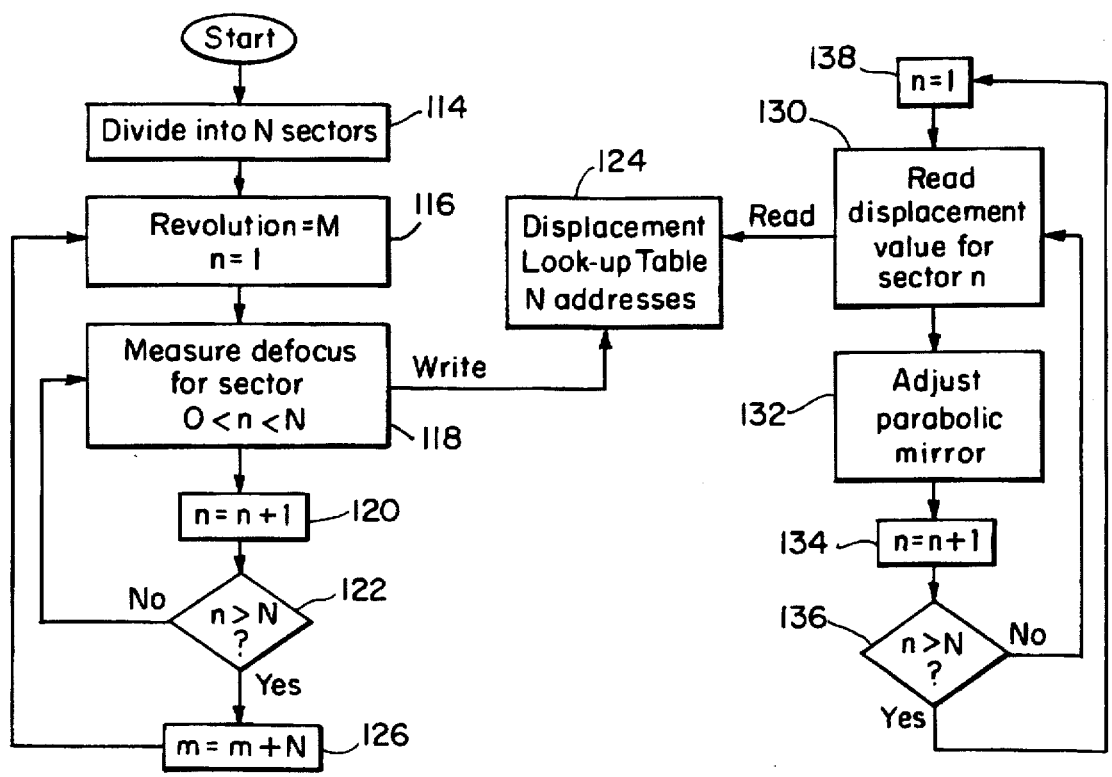
FIG. 6 is a flow chart of an alternative embodiment of the system depicted in FIG. 4 for the trace shown in FIG. 5.

The autofocus routine depicted in FIGS. 4 and 6 is a computerized routine 200, FIG. 7 which takes as input a revolution signal from air spindle encoder 14, FIG. 1 and a surface warpage or displacement signal from displacement sensor 34, FIG. 1, shown in block diagram form in FIG. 7. If the surface is divided into 32 sectors, a displacement look-up table 202 having 32 address spaces is created in computer memory. The autofocus routine both reads from and writes to displacement look-up table 202 and provides a focus control signal on line 204 to digital-to-analog converter 206 thereby providing a voltage signal to piezoelectric actuator 40 which adjusts parabolic mirror 28 to maintain the focus of the laser beam on the surface despite warpage and/or mechanical displacement due to movement of air spindle 18, FIG. 1.

Simply stated, the stored displacement value for each sector indicative of the warpage in that sector is only updated once during a number of M revolutions and yet the parabolic mirror is adjusted to account for any warpage in each sector during each revolution.

The displacement of the surface in a direction normal to the surface, either because of surface warpage or surface displacement, may be detected and measured by a variety of techniques including mechanical sensors, or preferably the system 300 shown in FIG. 8.

System 300, FIG. 8, for detecting displacement of a surface 10 in a direction normal to the surface includes first grating 304 and second grating 306. Light from source 305 passes through lens 307 and grating 304. There are means such as one half of the pupil of objective lens 308 for projecting an image about 0.5×1 mm of first grating 304 onto surface 10. The other half of the pupil of objective lens 308 and mirror 310 direct the secondary image of the first grating reflected from the surface onto second grating 306. This forms a fringe pattern after the secondary image passes through the second grating. The fringe pattern is monitored by detector 312 to detect displacement of surface 10 in a direction normal to the surface.

In a preferred embodiment, first and second gratings 304 and 306 are both Ronchi rulings (300 lines per inch). Second grating 306 is orientated with this rulings at an angle (e.g. 3°) with respect to the rulings of the image of the first grating reflected off the surface forming a moire tinge pattern created after the image of the first grating passes through the second grating. Any shift of the fringes of the moire pattern is indicative of the displacement of surface 12. Detector 312 is preferably a CCD camera aligned to detect any shift of the fringes the moire fringe pattern and to provide a signal indicative of the displacement of the surface in a direction normal to the surface.

If surface 10 is a patterned photolithographic mask then anamorphic means such as cylindrical lens 316 defocuses the secondary image of grating 304 reflected off surface 10 in a direction parallel to the direction of the rulings of the secondary image to blur the distinction in reflectivity of the surface while still preserving the focus of he secondary image in a direction perpendicular to the direction of the rulings. Blurring the image of the first grating reflected off the surface in a direction parallel to the rulings eliminates the sharp contrast in reflectivity due to a chrome/glass interface on the surface under inspection. A cylindrical lens blurs the image in that direction and maintains the sharpness of the image in the direction perpendicular to the rulings so the moire fringe pattern is not adversely affected. Cylindrical lens 316 is positioned in an optical path between surface 10 and second grating 306 and is orientated with its cylindrical axis perpendicular to the direction of the rulings of the image of first grating 304 reflected off surface 10. Cylindrical lens 316 has a very short focal distance to spread the image as wide as possible and enough of an aperture to intercept the entire beam reflected back through the second half of objective lens 308. Lens 316 may be a negative lens with a focal length of −20 mm, 20 mm wide.

Another cylindrical lens 318 is positioned in an optical path behind second grating 306 to concentrate more light onto detector 312. Cylindrical lens 318 is orientated with its cylindrical axis perpendicular to the direction of the fringes in the fringe pattern and has a short focal distance and enough of an aperture to intercept the entire width of grating 318. Cylindrical lens 312 is placed as close as possible to the second grating 306 in order that detector 312 can also be placed close to second grating 306 so that the fringes are sharply visible e.g., a positive lens with a focal length of 22 mm, 22 mm wide. Lens 318 squashes the fringes to concentrate more light onto CCD camera 312.

The routine for writing the displacement values to a look-up table stored in computer memory is explained with reference to FIGS. 4 and 6. The look-up table is only written once per M (e.g. 32) revolutions. The look-up table is read, however, for each sector, each revolution, and parabolic mirror 28 is adjusted by piezoelectric actuator 40, preferably a Polytek PI Inc., "Piezotranslator" P.845.20.

Implemented in surface inspection apparatus 5, FIG. 1, the surface displacement detection and adjustment system of this invention operates as follows.

The autofocus apparatus 34 essentially consists of two primary components. The sensor includes the optical system, a CCD line scan camera, described above with reference to FIG. 8, camera interface or frame grabber 220, signal processor 36, FIG. 1 and a software program disclosed below that provides information about the vertical position of the surface. The actuator includes a controller, a software program disclosed below that keeps track of the current position of rotary stage 18 and provides real rime control data for the piezoelectric actuator 40.

One air spindle stage revolution is divided into 32 angular sectors. At 1800 rpm, each sector takes about 1 ms to pass. The controller utilizes a table 86, FIG. 4 for the real time control. Processor 36, FIG. 1 keeps track of the current theta-position of the spindle using rotary encoder 14 (FIGS. 1 and 7) pulses (ticks) and updates the signal for piezoelectric actuator 40, FIG. 1 in real time for every angular sector. Table 86, FIG. 4 is an array that contains focus control values for all 32 sectors.

The data in the table is periodically updated by sensor 34. The translation speed is rather slow but that allows updates for the focus control values for each sector only once in M=32 revolutions of the surface when the illumination spot from laser beam 24 is located approximately in the same area on the plate for the given sector.

Sensor 34 works in a repetitive manner sequentially acquiring signals for the angular sector. The software program depicted in FIGS. 4 and 6, programmed on processor 36, keeps track of the current angular sector number in real time. It starts to acquire data for the next sector after the end of data processing for the previous one. To do so it triggers sensor 34 with the encoder pulse at the beginning of the sector being acquired. The CCD line image camera, FIG. 8 of sensor 34, FIG. 1 starts to integrate the light signal when passing the sector. At that time, the line scan camera output signal is ignored. The next encoder pulse comes at the border between the current sector and the next sector and it triggers a new line scan cycle. The camera output signal in that cycle represents the light accumulated in the previous one. That data is entered into the processor 36 through frame grabber for processing. The data processing for the acquired sector may take the time of one or several revolutions to produce a result: the new focus value to update the corresponding table element.

The rotary encoder pulses generate interrupt signals every 1/32 of the revolution. The interrupt handling of autofocus routine 200, FIG. 7, includes: indexing of the current sector numbering counter which is a real time ring counter implemented by the software reset by the rotary encoder index pulse; triggering of the line scan cycle; and selecting the table element that corresponds to the current sector number and sending the table focus value through D/A converter, 206, FIG. 7 to the actuator.

The autofocus data processing subroutine of autofocus routine 200, FIG. 7, includes the following procedures: data acquisition, data transition and correction; digital filter and signal analysis; and digital filtering. The data acquisition routine includes: indexing of the ring counter for the sector number to be acquired next; waiting for the current sector number to become equal to the sector number (current sector counter is equal to acquisition counter); waiting for the end of the scan line for the current sector (flag from the frame grabber); enabling the frame grabber for the snap of the data that will be obtained during the next sector; (those data represent the light signal accumulated when passing the current sector); and waiting for the end of acquisition (2K pixels, 12 bit word for every pixel). The data transition and correction routine includes: retrieving data sequentially from the buffer memory in the form of words (2K); verifying every word to find maximum and minimum signal values for the diagnostics; corrections of the words (dark level correction) by adding a corresponding bias value from the calibration data table (fixed point operation); correcting the every word (non-uniformity correction) by multiplying it with a corresponding scale value from the calibration data table (float point operation); and transferring data sequentially to the computer memory in the form of 16 bits words (2K) for use as input data for digital filtering (convolution). The digital filter and signal analysis processing procedure includes: calculation of the output digital filter data for the analysis windows; verifying the output data to find maximum and minimum values for the diagnostics; finding the pair of pixel points in the vicinity of the plus-to-minus-zero crossing inside the analysis window; linearly interpolating between the above points and calculation of the precise zero-crossing position; and calculating the final result focus position for the table updating by linear transformation and correction of the obtained zero-crossing.

The software for implementing the flow chart depicted in FIG. 4 is as follows:

```
// 12 bit camera - Enc. Synch. Horiz. mode, Software Trigger for Data Acqusition // Generates digital output pulse - bit PB0 (PIO-12) with an active
// acquisition status (AQSTAT)

// (Dark signal and nonuniformity of CCD correction )

// performs autofocus data acquisition in Encod. Sync. endless loop (unless
// any key is pressed) and runs signal processing (signal correction,
// convolution, defocus calculation, max_out and AFCT
// update) for sequential sectors.

// Generates Software trigger every revolution for the next sequent. sector.

// USE: for autofocus test.  [ Handshaking  with the Encoder Board. ]

// Synchronization with encoder pulses (ticks - NUM_SECTORS per revolution)
// and Index pulses.
// Every next revolution acquires the next sequential sector. This cycle
// takes NUM_SECTORS+ revolutions to create (update) the array "result[]" - the
// Autofocus Control Table. Last sectors may require additional idle
// revolutions to process and then synchronize with the coming Index.

// Writes the current array "result[]" into the next sequential data file
// (text format) n.dat every time any letter key is pressed.

// Encoder pulses (ticks) bit C0 at PIO-12, Index pulse - bit C1.
// Handshaking reset output bit PB1.

// Provides fast data transfer between VRAM and the host RAM because of using
// function rap_vram_read  ( accesses vram via pointer),
// it DOES print max_out
// here sig_raw[] is array of shorts ( 12 bit signal from the camera ) !

// AS, 06/21/95

//#define _C32
#include <rap.h>
#include <rapmsg.h>
#include <rapreg.h>
#include <dosvid.h>
#include <stdio.h>
#include <stdlib.h>
#include <string.h>
#include <conio.h>
#include <math.h>
#include <dos.h>
include <i86.h> define TIMEOUT       0x100000L    /* Frame Grabber timeout  */
define FACTOR        1024      /* factor of signal reduction */
#define SATURATION    4095              /* saturation level */
#define MIN_MAXOUT    240000  /* threshold for good max_out */
```

```c
#define RAPTOR_INITIAL_DE    2        /* delay , s  nds */
#define MIN_HRESET           0xaa0    /* minimum HL_ET */
                                      /* for encoder sync. */
define F_RUN_HRESET         0xcd0 define FILENAME_D           "darf.dat"
define FILENAME_NOUN        "noun.dat"
#define FILENAME_IN          "dalsa.dat"
#define FILENAME_OUT         "out_win.dat"

#define FREERUN_MODE         0  /* FreeRun Horizontal & Vertical */
#define FREE_TRIG_MODE       1  /* FreeRun Horizontal &         */
                                /* Software Trig. Vertical */
#define ENC_FREE_MODE        2  /* Encoder Synch. Horizontal &  */
                                /* FreeRun Vertical */
#define ENC_TRIG_MODE        3  /* Encoder Synch. Horizontal &  */
                                /* Software Trig.Vertical */ define ESC                  27       /* Escape from keyboard    */
define DAC_BASE_ADDR        0x300
define PIO_BASE_ADDR        0x280 define START_WIN            1755     /*= starting pixel of window */
                                      /* of interest =*/ define K                    53       /*= number of pixels per */
                                      /* half period of the FIR =*/ define M                    15       /*= number of cycles in */
                                      /* recursion formula =*/ define WIN_SIZE             94       /*= window of interest size in pixels define OFFSET               0        /*= defocusing offset =*/ define SENSITIVITY          .25      /*= ratio of defocusing signal to */
                                      /* one pixel displacement =*/
define NUM_SECTORS          32 define FILENAME_OUT_BEG     "c:\\watcom\\as\\dat\\"
define START_FILE_NUMBER    1        /* will be like 0001.dat */
define MAX_FILE_NUMBER      16 define RESET_DURATION       10 /* reset pulse duration */ define CLAMP_SECTOR         0  /* sector number to clamp DAC output */ int raptor_start(int mode);                              /*= prototype =*/
int initialization();                                    /*= prototype =*/
int acqure_pulse_time_check(long tmt);                   /*= prototype =*/ int read_correct(int cor1_ar[], int cor2_ar[], int dest_ar[], int no);
                                                         /*= prototype =*/ void set_dac_b10(float volts, int channel);              /* prototype */
int zero_crossing( long array_out[]);                    /*= prototype =*/
void write_in(char *filename, int *array, int nn);       /*= prototype =*/
float convolve( int lngth, int start_win);               /*= prototype =*/
```

```c
float snap_focus();                                      /*= prototype =*/
int read_data(char *filename, int array_dat[] );         /*= prototype =*/
long find_max(long array_check[]);                       /*= prototype =*/
void write_float_in(char *filename, float *array, int nn); /*= prototype =*/
int get_index();                                         /*= prototype =*/
int get_tick();                                          /*= prototype =*/
void reset();                                            /*= prototype =*/
void bell(int freq, int dur);                            /*= prototype =*/
char get_yesno();                                        /*= prototype =*/ static RAPTOR board;
static unsigned short sig_raw[2048];
static long sig_out[2048], fir[2048], tog_2[50];
static int sig_in[2048];
static int dark_in[2048];
static int noun_in[2048];
static int conv_lngth, start_win=START_WIN;
float  result[NUM_SECTORS] = {0};
static char instr[40];

void main()
{ int sector, rev, filenumber;
  int clamp_sector = CLAMP_SECTOR;
  char       inpkey = NULL;
  char yes_no = 0;
  char filename_out[40] = ("");
  char number_convert[10];

if( initialization())
     exit(1);

do
  {
     while( !yes_no)           /*= get value for clamp_sector =*/
     {
        printf( "Sector to clamp the DAC output = %d\n", clamp_sector);
        printf( "\ndo you want to choose another sector? y/n \n");
        yes_no = get_yesno();
        if( yes_no == ESC)
              exit(1);
     }
     if( yes_no == 'Y')
     {
        printf( "enter the new number\n");
        gets( instr);
        clamp_sector = atoi( instr);
        if( ( clamp_sector < 0 ) || ( clamp_sector >= NUM_SECTORS ))
           printf("Wrong sector number! Please try again\n");
     }
  }
  while( ( clamp_sector < 0 ) || ( clamp_sector >= NUM_SECTORS ) );
  printf("36;40;1m\n");
  printf( "Clamp DAC sector number = %d\n", clamp_sector);
  printf("\n");
  printf("Running... Press any letter key to write data into the next *.dat file
  printf("or press ESC to exit\n");
```

```c
    printf("33;1m\n");
    delay(2500);
    for( filenumber=START_FILE_NUMBER; filenumber < MAX_FILE_NUMBER+1; filenumber+
    {
        while( !kbhit())
        {
            for( rev=0; rev<NUM_SECTORS; rev++)
            {
                while( !get_index());  /* wait for beginning of index pulse */
                rap_con_aq( board, RAPCON_SNAP); /*= tells board to snap a frame =*/
                sector=0;
                while( sector != rev)
                {
                    reset();              /* ending of index or enc. pulse */
                    sector+=1;
                    while( !get_tick()); /* wait for begin. of next enc pulse */
                }
                reset();                  /* ending of enc pulse or index */ result[rev]=snap_focus(); /* snap frame and processing */
                if( rev == clamp_sector)
                {
                    if( (result[rev] != -1000) && (result[rev] != -10000))
                        set_dac_b10((result[rev])/2, 0);  /* sets bipolar 0+/-10V to DA
                }
                reset();    /* need to reset index in case of idle revolution */

} /* end for.. rev */

} /* end while( !kbhit()) */ inpkey = getch();
        if( inpkey == 27)
            break;
        sprintf(number_convert, "%04d", filenumber);
        strcpy(filename_out, FILENAME_OUT_BEG);
        strcat(filename_out, number_convert);
        strcat(filename_out, ".dat");
        write_float_in(filename_out, result, NUM_SECTORS);
        printf("Data file %s has been created\n", filename_out);
        bell(500,750);

} /* end for...filenumber */ printf("37;40;0m\n");

if( filenumber == (MAX_FILE_NUMBER+1) )
        printf("Cycle is over. Number of data files written is %d\n", filenumber-1
    rap_sys_close();                /*= free frame grabber resources =*/

} /* end main */ float snap_focus()
{ float defoc, ret_value=0;
    int status = 0;
    long max_out;
```

```
    rap_con_trig(board);  /* start acquire with software trigger  */
    acqure_pulse_time_check(TIMEOUT);
    rap_message_filter( RAPMSG_UNALIGNED_XFER, RAPMSG_IGNORE);
                                                    /*= suppress warning =*/
    rap_vram_read(board, 0, 4096, sig_raw); /*= copy pixels to host buffer =*/ read_correct(dark_in, noun_in, sig_in, 2048);

defoc = convolve( conv_lngth, start_win);  /*= perform math and find zero cros
    if( defoc == -10000 )                      /* no crossing was found */
    {
        status = 1;
        ret_value = defoc;
    }
    max_out = find_max(sig_out);   /*= maximum value in sig_out =*/
    if( max_out <= MIN_MAXOUT )
    {
        printf( "Too low output of the Digital Filter\n");
        status = 2;
        ret_value = -1000;
    }
    printf( "%d\n", max_out);

//      write_in(FILENAME_OUT, sig_out, WIN_SIZE);

if( !status)
    {
        ret_value = 2*defoc;
    }
    return ret_value;
} /* end snap_focus */ int initialization()
{
    int i, ret=0;

// Preparing arrays for the Digital filter conv_lngth = min( start_win, 2*M*K-1);  /*= which signal is shorter? =*/
                                            /* find the overlap area    */
    for( i=0; i<=conv_lngth; i++)
        fir[i] = pow( -1, i/K);  /* build Digital Filter Response */
                                 /* for the straight formula      */
    for( i=1; i<2*M; i++)
        tog_2[i] = 2*pow( -1, i);  /* array for Recursion Formula */

/**************************************************************/

/* PIO-12 Board initialization. Mode 0. Control word 99Hex:  */
        /* A - input, B - Output, C - Input  */ outp(PIO_BASE_ADDR+3, 0x99);
    outp(PIO_BASE_ADDR+1, 0x0);  /* sending zero to Port B  */
    reset();

/**************************************************************/
```

```c
    if( read_data(FILENAME_ , dark_in) != 2048 ) /* read dark data */
    {
        printf( "bad dark data file\n");
        ret=1;
    } if( read_data(FILENAME_NOUN, noun_in) != 2048 ) /* read n_unif. data */
    {
        printf( "bad nonuniformity data file\n");
        ret=2;
    } if( raptor_start(ENC_TRIG_MODE) != 0 )
    ret=3;
    return ret;

} /* end initialization() */ int read_data( char *filename, int array_dat[])
{
    FILE *p_input;
    char file_line[40];
    int cnt=0;

p_input = fopen( filename, "rt");    /*= read, text =*/
    if( p_input == (FILE *)NULL)
    {
        printf( "cannot open calibration data file\n");
        exit( 1);
    }
    while( fgets( file_line, 20, p_input) != NULL)   /*= read to end of file =*/
    {
        array_dat[cnt] = atol( file_line);    /*= convert column to integers,
        cnt++;
    }
    fclose( p_input);
    return( cnt);    /*= number of lines read =*/
} void write_in(char *filename, int *array, int nn)
{
    FILE *p_file;
    int i;

p_file = fopen( filename, "wt");    /*= write, text =*/
    if( p_file == (FILE *)NULL)
    {
        printf( "cannot open output file\n");
        exit( 1);
    }
        for( i=0; i<nn; i++)
    {
            fprintf( p_file, "%d\n", array[i]);    /*= write to file =*/
    }
    fclose( p_file);
} int raptor_start(int mode)
{
```

```
    void hreset_program(int nr_val);    /* prototype */ printf("Data Raptor initialization...\n");

if( rap_sys_open( BFNULL, RAPSYS_INIT) < RAPOK)
    {
        printf("cannot start Data Raptor\n");
        return -1;
    }
    board = rap_board_handle(0);    /*= first and only board in system =*/
    rap_con_clockfreq(board, RAPCON_10MHZ);
    switch (mode)
    {
        case FREERUN_MODE:
            rap_con_hmode(board, RAPCON_FREERUN);
            rap_con_vmode(board, RAPCON_FREERUN);
            hreset_program(F_RUN_HRESET);
            break;
         case FREE_TRIG_MODE:
            rap_con_hmode(board, RAPCON_FREERUN);
            rap_con_vmode(board, RAPCON_ONESHOT);
            hreset_program(F_RUN_HRESET);
            break;
          case ENC_FREE_MODE:
            rap_con_hmode(board, RAPCON_ONESHOT);
            rap_con_vmode(board, RAPCON_FREERUN);
            hreset_program(MIN_HRESET);
            break;
           case ENC_TRIG_MODE:
            rap_con_hmode(board, RAPCON_ONESHOT);
            rap_con_vmode(board, RAPCON_ONESHOT);
            hreset_program(MIN_HRESET);
            break;
          default:
            break;
    } /* end switch  */
    sleep(RAPTOR_INITIAL_DELAY);
    printf("Raptor OK\n");
    return 0;

} /* end raptor_start  */ void hreset_program(int hr_val)
{

// to freeze CTAB rap_reg_poke(board, RAPREG_CTABHOLD, 1);

//make sure entire table is empty rap_ctab_fill(board, 0x0000, 0x2000, RAPHCTAB_HRESET, 0);

//program the HRESET pulse rap_ctab_fill(board, hr_val, 0x0001, RAPHCTAB_HRESET, (UINT) -1);

// to enable CTAB
```

```c
    rap_reg_poke(board, RAPREG_CTABHOLD, 0);
} /* end hreset_program */ int acqure_pulse_time_check(long tmt)
{
    long timeout;
    int ret = 0;

/*= wait for acquisition to begin =*/ timeout = tmt;
    while( rap_reg_peek( board, RAPREG_AQSTAT)==0 && timeout>0L) timeout--;
    if( !timeout)
    {
        printf("Timeout for the acquisition to begin\n");
        ret = 1;
    }
            /*= wait for the acquisition to end =*/ timeout = tmt;
    while( rap_reg_peek( board, RAPREG_AQSTAT)!=0 && timeout>0L)
    {
        timeout--;
        outp(PIO_BASE_ADDR+1, 0x1); /* Start a Pulse, Pulse is present */
    }
    if( !timeout)
    {
        printf("Timeout for the acquisition to accomplish\n");
        if( ret == 0 )
            ret = 2;
        else
            ret = 3;
    }
    outp(PIO_BASE_ADDR+1, 0x0);  /* Stop a Pulse */
    return ret;
} /* end acqure_pulse_time_check      */ int read_correct(int cor1_ar[], int cor2_ar[], int dest_ar[], int no)
{
    int i;
    int ret = 0;

for( i=0; i<no; i++)
    {
        if( sig_raw[i] >= SATURATION )
        {
            printf("Camera Signal saturation: pixel# = %d\n", i);
            ret =1;
        }

/* type conversion below (from unsigned short to int) is implicit */ dest_ar[i] = (sig_raw[i]-cor1_ar[i])*cor2_ar[i]/FACTOR;
    }
    return ret;
```

} /* end read_correct */

```c
float convolve( int lngth, int start_win)
{
    int i, j, index, temp_ind;
    long temp;
    float z_cross, a, b, defocus;

temp=0;
    /*= straight convolution, up to and including START_WIN =*/
    for( i=0; i<=lngth; i++)
        temp += sig_in[start_win-i] * fir[i];
    sig_out[0] = temp;        /*= first element of output signal =*/

/*= recursion formula, begins at START_WIN + 1 =*/
    for( i=1; i<=WIN_SIZE; i++)
    {
        temp = sig_in[i+start_win];              /*= first undoubled term
        for( j=1; j<2*M; j++)                    /*= doubled terms, alter
        {
            temp_ind = i+start_win-j*K;
            if( temp_ind >= 0)      /*= stay with in sig_in bounds =*/
                temp += tog_2[j] * sig_in[temp_ind];
        }
        temp_ind -= K;
        if( temp_ind >= 0)      /*= stay within sig_in bounds =*/
            temp += sig_in[temp_ind];            /*= add final undoubled term
        sig_out[i] = sig_out[i-1] + temp;        /*= combine with previous output
    }
    if( (index = zero_crossing( sig_out)) != NULL)
    {
        /*= linear interpolation =*/
        a = (float )sig_out[index];              /*= distance above zero =*/
        b = (float )labs( sig_out[index+1]);     /*= distance below zero =*/
        z_cross = index - WIN_SIZE/2 + a/(a + b) + 0.5;
        defocus = (z_cross + OFFSET)*SENSITIVITY;
        return defocus;
    }
    else
    {
        printf( "no crossing found\n");
        return -10000;
    }
} int zero_crossing( long array_out[])   /*= look for sign change =*/
{
    int i;
    for( i=0; i<WIN_SIZE; i++)
        if( array_out[i] > 0 && array_out[i+1] <= 0)
            return i;      /*= array index just before zero crossing =*/
    return NULL;           /*= no crossing found =*/
} void set_dac_b10(float volts, int channel)   /* sets bipolar 0+/-10V */
```

```c
{                                                /* to the ...C-02 board */
    float sig_out;
    int highbyte, lowbyte;

if ((volts >= -10) && (volts <= 10))
            sig_out = volts*(-204.7)+2048;
        else                                /* Saturation if out of range */
        {
            if ( volts < -10 )
                sig_out = 4095;
            else                    /* volts >10 */
                sig_out = 0;
        } highbyte = sig_out/16;                          /* Convert to High Byte */
    lowbyte = 16*(sig_out-highbyte*16);             /* Convert to Low Byte */
    outp(DAC_BASE_ADDR+channel*2, lowbyte);         /* Write Low Byte */
    outp(DAC_BASE_ADDR+channel*2+1, highbyte);      /* Write High Byte */

} /*  end set_dac  */ long find_max(long array_check[])    /*= look for maximum in output array =*/
{
    int i;
    long temp, max=0;
    for( i=0; i<WIN_SIZE; i++)
    {
        temp = abs( array_check[i]);
        if( temp > max)
            max = temp;
    }
    return max;
} void write_float_in(char *filename, float *array, int nn)
{
    FILE *p_file;
    int i;

p_file = fopen( filename, "wt");     /*= write, text =*/
    if( p_file == (FILE *)NULL)
    {
        printf( "cannot open output file\n");
        exit( 1);
    }
    for( i=0; i<nn; i++)
    {
        fprintf( p_file, "%f\n", array[i]);     /*= write to file =*/
    }
    fclose( p_file);
} int get_tick()    /* Reads the Port C of the PIO-12 board */
{
    int prt_c, ret=0;

prt_c = inp(PIO_BASE_ADDR+2);
    if( (prt_c == 1) || (prt_c ==3))
```

```
            ret=1;
    return ret;

} /* end  get_tick  */ int get_index()    /* Reads the Port C of the PIO-12 board */
{
    int prt_c, ret=0;

prt_c = inp(PIO_BASE_ADDR+2);
    if( prt_c == 3)
         ret=1;
    return ret;

} /* end  get_index  */ void reset()    /*= sending a short handshaking RESET pulse bit PB1 =*/
{
    int timeout;

outp(PIO_BASE_ADDR+1, 0x2); /* Start a Pulse, Pulse is present */
    timeout = RESET_DURATION;
    while( timeout > 0 ) timeout--;
    outp(PIO_BASE_ADDR+1, 0x0);  /* Stop a Pulse  */

} /* end reset  */ void bell(int freq, int dur)
{
    sound(freq);
    delay(dur);    /* milliseconds */
    nosound();
} char get_yesno()
{
    char kbin;

kbin = getch();
    switch( kbin)
    {
        case 'Y':
            return 'Y';
            break;
        case 'y':
            return 'Y';
            break;
        case 'N':
            return 'N';
            break;
        case 'n':
            return 'N';
            break;
```

```
        case ESC:
            return ESC;
            break;
        default:
            return 0;
            break;
    }
} /* end get_yesno   */
```

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A surface displacement detection and adjustment system comprising:

means for inspecting a surface;

means for detecting displacement of the surface in a direction normal to the surface;

means for dividing the surface into N sectors;

means, responsive to said means for detecting, for calculating the amount of displacement of said surface in each sector of the surface;

a displacement value look-up table; and means, responsive to said means for calculating, for writing a displacement value for a each sector to said table once per M cycles, and means, responsive to said look-up table, for adjusting said means for inspecting in each cycle.

2. The system of claim 1 further including means for averaging a present displacement value for a given sector N with a previously calculated displacement value for that sector and for writing the average to the table for reducing noise and interference.

3. The system of claim 1 in which said means for writing writes the displacement value for all N sectors during one cycle, M-1 cycles before the next write operation.

4. The system of claim 1 in which said means for writing writes a displacement value at a rate of one sector per cycle.

5. The system of claim 1 in which said table has N address spaces.

6. The system of claim 5 in which each address space is allocated for a specific sector.

7. The system of claim 1 in which said means for inspecting includes a laser beam source and means for focusing a laser beam from said source on the surface.

8. The system of claim 7 in which said means for adjusting adjusts said means for focusing.

9. The system of claim 1 in which means for detecting includes:

a first grating;

a second grating; .

means for projecting an image of the first grating onto the surface;

means for directing a secondary image of the first grating reflected off the surface onto a second grating; and detector means, responsive to a fringe pattern formed after said secondary image passes through said second grating, for detecting displacement of said surface in a direction normal to the surface.

10. A surface displacement detection and adjustment system comprising:

means for inspecting a surface;

means for detecting displacement of the surface in a direction normal to the surface as the surface revolves;

means for dividing the surface into N sectors;

means, responsive to said means for detecting, for calculating the amount of displacement of said surface in each sector of the surface as it revolves;

a displacement value look-up table; and means, responsive to said means for calculating, for writing a displacement value for each sector to said table once per M revolutions.

11. The system of claim 10 further including means for averaging a present displacement value for a given sector N with a previously calculated displacement value for that sector and for writing the average to the table for reducing noise and interference.

12. The system of claim 10 in which said means for writing writes the displacement value for all N sectors during one revolution, M-1 revolutions before the next write operation.

13. The system of claim 10 in which said means for writing writes a displacement value at a rate of one sector per revolution.

14. The system of claim 10 in which said table has N address spaces.

15. The system of claim 14 in which each address space is allocated for a specific sector.

16. The system of claim 10 in which said means for inspecting includes a laser beam source and means for focusing a laser beam from said source onto the surface.

17. A surface displacement detection and adjustment system comprising:

a laser beam source and means for focusing said laser beam source on the surface, said means for focusing being adjustable with respect to said surface;

means for detecting displacement of the surface in a direction normal to the surface as the surface revolves;

means dividing the surface into N sectors;

means, responsive to said means for detecting, for calculating the amount of displacement of said surface in each sector of the surface as it revolves;

a displacement value look-up table; and means, responsive to said means for calculating, for writing to said table a displacement value for a given sector N once per M revolutions.

18. The system of claim 17 further including means for averaging a present displacement value for a given sector N with a previously calculated displacement value for that sector and for writing the average to the table for reducing noise and interference.

19. The system of claim 17 in which said means for writing writes the displacement value for all N sectors during one revolution, M-1 revolutions before the next write operation.

20. The system of claim 17 in which said means for writing writes a displacement value at a rate of 1 sector per revolution.

21. The system of claim 17 in which said table has N address spaces.

22. The system of claim 21 in which each address space is allocated for a specific sector.

23. The system of claim 17 further including means for reading said look-up table.

24. The system of claim 18 further including means for reading each displacement value stored in said look-up table every revolution.

25. The system of claim 17 further including means, responsive to said means for reading, for adjusting said means for focusing on every sector as said surface revolves.

* * * * *